US006593276B2

(12) United States Patent
Walley et al.

(10) Patent No.: US 6,593,276 B2
(45) Date of Patent: Jul. 15, 2003

(54) ROOT CONTROL COMPOUND

(76) Inventors: James V. Walley, K & W Enterprises, 1100 Mississippi Dr., Waynesboro, MS (US) 39367; Tommy Kelley, P.O. Box 481, Waynesboro, MS (US) 39367

( * ) Notice: Subject to any disclaimer, the term of this patent is extended or adjusted under 35 U.S.C. 154(b) by 0 days.

(21) Appl. No.: 10/025,608

(22) Filed: Dec. 26, 2001

(65) Prior Publication Data

US 2002/0147112 A1 Oct. 10, 2002

Related U.S. Application Data

(60) Provisional application No. 60/263,515, filed on Jan. 24, 2001.

(51) Int. Cl.$^7$ .......................... A01N 25/34; A01N 59/16; A01G 9/00
(52) U.S. Cl. .......................................... 504/187; 47/65.7
(58) Field of Search ............................ 504/187; 47/65.7

(56) References Cited

U.S. PATENT DOCUMENTS

| | | | | |
|---|---|---|---|---|
| 2,848,842 A | 8/1958 | Tennant, Jr. | | 47/34 |
| 3,356,483 A | 12/1967 | Leasure et al. | | 71/66 |
| 3,582,312 A | 6/1971 | Hess et al. | | 71/27 |
| 4,012,503 A | 3/1977 | Freiman | | 424/145 |
| 4,972,627 A | 11/1990 | Hori et al. | | 47/64 |
| 5,162,488 A | 11/1992 | Mason | | 528/275 |
| 5,335,449 A | * 8/1994 | Beatty | | 47/48.5 |
| 5,451,242 A | 9/1995 | Ming et al. | | 71/36 |
| 5,526,607 A | 6/1996 | Roesch et al. | | 47/66 |
| 6,114,431 A | 9/2000 | Lee et al. | | 524/435 |

FOREIGN PATENT DOCUMENTS

GB 2 110 518 6/1983

OTHER PUBLICATIONS

Tatum, D., Matta, F., and Johnson, K, "Rooting–Out Control in Pot–in–Pot Production", *Southern Nursery Association Research Conference*, 1999, vol. 44, pp. 29–33.

* cited by examiner

*Primary Examiner*—S. Mark Clardy
(74) *Attorney, Agent, or Firm*—Richard C. Litman

(57) ABSTRACT

A root control composition comprising zinc or a compound of zinc, in latex or other suitable binder. The composition may be painted, sprayed, injected, or molded into a container or fabric to prevent root circling of ornamental plants. Also, devices that might use this composition include weed barriers, grow bags, mats, nursery containers, nursery pots, and flats. The present inventive compositions also act as a micro nutrient, in plants, affecting cell elongation while encouraging cell division. The useful range of compositions is from about 3% to about 28% zinc by weight of zinc compound in a binder such as latex paint, and the preferred range is about 14% zinc in a carrier.

16 Claims, No Drawings

ROOT CONTROL COMPOUND

CROSS-REFERENCE TO RELATED APPLICATION

This application claims the benefit of U.S. Provisional Patent Application Serial No. 60/263,515, filed Jan. 24, 2001.

BACKGROUND OF THE INVENTION

1. Field of the Invention

The present invention relates generally to horticulture, and, more specifically, to a coating formulation useful in the root control of plants.

2. Description of the Related Art

It is known to employ chemical formulations for root control of plants for use in construction of containers for plants, and for use in the earth for purposes of providing a barrier to tree roots and the like for concrete sidewalks and building foundations, etc. Present formulations employ elemental copper in a finely divided state or copper compounds. Copper suffers from relatively high cost and unstable price; also, it is relatively environmentally unfriendly.

British Patent document GB 2 110 518 A, published Jun. 22, 1983, describes a bioactive coating and fixing composition useful for spraying or coating plant seeds or plant leaves. The material contains at least one reversibly water-soluble protein of natural origin and at least one non-phytotoxic salt or complex of various metals, including Zn, Mg, Co, Fe, Mn, Cu, Ti and Mo. The aqueous solution forms, after drying, a water insoluble film which, due to its structure, accelerates and intensifies the germination of seeds. The coating, when applied to plant leaves, such as by spraying, acts as a biocide, protecting against fungus and pests. The compounds of the British Patent are not intended for root control.

U.S. Pat. No. 2,848,842, issued Aug. 28, 1956, to Tennant, Jr., describes a plant container having fibrous walls holding a root inhibitor, such as zinc oxide. Example 2, thereof, describes a mixture of di-beta-naphthyl-p-phenylene diamine, zinc oxide, and neoprene latex to be incorporated within the fibrous walls. The '842 patent does not teach to use of a coating for root control which is applicable to plant containers and cloth material.

U.S. Pat. No. 3,356,483, issued Dec. 5, 1967 to Leasure, et al., describes the use of divalent heavy metal(including copper and zinc) containing compounds to discourage growth of unwanted plants and fungus. The compounds can also be used, depending on the concentration, to promote plant growth and hasten the maturating and ripening of grain, vegetable, and fruit crops. Also described is the use of the compounds in coatings such as latex paint to protect against mold or mildew. Also, the compounds can be distributed in textiles or cellulosic materials to protect against mildew and rot. The '483 patent does not describe such compounds in a coating such as with latex paint for use in plant root control.

U.S. Pat. No. 5,526,607, issued Jun. 18, 1996, to Roesch et al. describes a delivery system or device in the form of a cup or pot that delivers biocide or fertilizer. The device comprises a composition that includes cellulose ether, zinc stearate, and cellulose tissue fiber. The '607 patent does not describe any composition or delivery system for root control of plants.

U.S. Pat. No. 3,582,312, issued Jun. 1, 1971, to Hess et al. describes the use of zinc as a micro nutrient. The '312 patent does not teach the use of zinc for root control of plants.

U.S. Pat. No. 4,012,503, issued Mar. 15, 1977, to Freiman, describes an anti fouling coating composition for marine use employing zinc oxide as an active component. The '503 patent does not teach the use of zinc for root control of plants.

U.S. Pat. No. 4,972,627, issued Nov. 27, 1990, to Hori et al. describes a sheet material for cultivating plants, employing elemental zinc or other metal, but does not describe the reason for the use of the metal as being for root control.

U.S. Pat. No. 5,451,242, issued Sep. 19, 1995, to Ming, et al. describes the use of zinc as a micro nutrient in synthetic soils for lunar use, but does not describe zinc as useful for plant root control.

U.S. Pat. No. 6,114,431, issued Sep. 5, 2000, to Lee et al. describes a plastic composition for forming plant containers. The composition contains a copper hydroxide or copper carbonate as an active root control agent. One embodiment of the composition contains up to 5% zinc and/or other nutrient metals in addition to the copper to buffer the toxicity of the copper and provide a more robust plant, but fails to teach the use of zinc in the absence of copper as a root control composition.

The Tatum et al. article teaches the use of a 2% zinc in latex paint composition on cloth for root control of container-grown plants to control the growth of roots through the container wall. The Tatum et al. article fails to teach the use of zinc to prevent root circling.

None of the above inventions and patents, taken either singularly or in combination, is seen to describe the instant invention as claimed. Thus, a root control compound solving the aforementioned problems is desired.

SUMMARY OF THE INVENTION

The present invention is a root control composition comprising zinc or a compound of zinc, in a latex or other suitable binder or carrier. The composition may be painted, sprayed, injected, or molded into a container or fabric to prevent root circling of ornamental plants. Also, devices that might use this composition include weed barriers, grow bags, mats, nursery containers, nursery pots, and flats. The useful range of compositions is from about 3% to about 28% zinc by weight of zinc compound in a binder or carrier such as latex paint, and the preferred range is about 14% zinc.

Accordingly, it is a principal object of the invention to provide a root control composition for use with plants having a zinc compound as the active ingredient.

It is another object of the invention to provide a root control composition as above having latex paint as a binder or carrier It is a further object of the invention to provide a root control composition as above which is useful for preventing root circling ornamental plants.

Still another object of the invention is to provide a root control composition as above which provides for a healthier plant with superior root systems than present root control compositions.

Still another object of the invention is to provide methods of manufacture or treatment of nursery pots to provide them with root control characteristics.

It is an object of the invention to provide improved compositions, methods, and articles of manufacture for the purposes described which are inexpensive, dependable and fully effective in accomplishing its intended purposes.

These and other objects of the present invention will become readily apparent upon further review of the following specification.

DETAILED DESCRIPTION OF THE PREFERRED EMBODIMENTS

The present invention is a root control composition comprising zinc or a compound of zinc, in latex or other suitable carrier. The composition may be painted, sprayed, injected, or molded into a container or fabric to prevent root circling of ornamental plants. Also, devices that might use this composition include weed barriers, grow bags, mats, nursery containers, nursery pots, and flats. The present inventive compositions also act as a micro nutrient, in plants, affecting cell elongation while encouraging cell division. Zinc is also useful as a fungicide.

The price of zinc is more stable and less expensive than currently available copper root pruning compositions. The price is related to availability, ease of processing, and environmental friendliness. Taking all of these qualities in consideration, zinc is a more economical product than copper.

The inventive zinc root control composition encourages branching of plant roots, and discourages root circling in containers and plant bags, thus enhancing the growth of ornamental trees, shrubs, and bedding plants.

Other applications of the inventive zinc root control composition include situations where pavement buckling is a problem from roots of plants and root clogging of septic tanks, field lines, buckling sidewalks, and cracking of building foundations. Various formulations of the inventive composition are contemplated for a variety of application needs, depending on factors such as the length of time root control is desired, and the prevailing weather, the composition of the soil, including soil pH, and various nutrients, water alkalinity, and the species of plant to be treated.

The following example illustrates the use of the inventive composition and method of its use.

EXAMPLE 1

The following tests were carried out by Dr. David Tatum of Mississippi State University, under the direction of Mr. James V. Walley.

Treatments:

The compositions of treatments employed were 7% ZnCl2, 14% ZnCl2, 28% ZnCl2, and 70% ZnCl2, each being a weight percent in pigment free, white, interior flat latex paint, designation No. A6W16 obtained from the Sherwin-Williams company. Also employed for comparison purposes was Spin Out®, a commercially available copper hydroxide from the Lerio Company, $Cu(OH)_2$, in latex paint having about 7% copper by weight, and used as a root control treatment.

Control treatments included latex paint only, and no treatment.

Species Used:

Species used were A. Begonia "cocktail Brz Gin", B. Impatiens "Pacifica Punch", and C. Vinca "Accent Mystic Mix".

Procedures:

Planted 6 plants in each treatment for a total of 21 plants in 4" pots, using Metro Mix 700® growing medium, fertilized through irrigation system with Peters Peat-lite® 20-10-20 at 100 ppm for first two weeks until plugs became established. Increased concentration to 200 ppm after week # 2. A Split-plot design was used, with individual plants chosen at random within the plant variety groups. An example of Split-Plot Design is as follows in Table No. 1, below:

TABLE 1

Split Pot Design

| | | |
|---|---|---|
| NT A1 | NT B2 | NT C4 |
| NT A7 | NT B6 | NT C1 |
| NT A2 | NT B5 | NT C3 |
| NT A4 | NT B1 | NT C2 |
| NT A6 | NT B3 | NT C7 |
| NT A3 | NT B4 | NT C3 |
| NT A5 | NT B7 | NT C6 |

Codes:

A-Begonia; B-Impatiens; C-Vinca

NT A1(No treatment Begonia Plant #1)

SO A-1(Spin Out® Begonia Plant #1)

LA-1(Latex paint Begonia Plant #1)

7ZnCl2 A-1(7% Zinc Chloride Begonia Plant #1)

14ZnCl2 A-1(14% Zinc Chloride Begonia Plant #1)

28ZnCl2 A-1(28% Zinc Chloride Begonia Plant #1)

Research Process:

Zinc Chloride was used as the zinc treatment of choice in this text. The ultimate goal of the test was to find a zinc compound that would offer results that were as good as or better than the Spin Out® treatments. Another goal was to find a zinc compound that would be readily released by latex paint.

Tests were run to compare Zinc Chloride from latex paint compared to other forms of zinc. These tests were conducted on 4% ZnCl2, 6% ZnO carbonate, 6% ZnO, 6% ZnCl2, and 6% Zinc Acetate. The 4% ZnCl2 and the 6% ZnCl2 were released at a much larger rate than any of the other forms tested. The release rates were as follows:

4% ZnCl2–110 mg/L Zinc; 6% ZnCl2–170 mg/l Zinc; 6%ZnO Carbonate-74 mg/l Zinc; 6% ZnO-120 mg/l Zinc; 6% Zinc Acetate-85 mg/l Zinc.

Based on these findings and the fact that the Spin Out® product had a 7% solution of Copper Hydroxide, it was decided to use the treatment levels mentioned earlier. Starting with a 7% ZnCl2 solution to have a level equal to the copper solution this level was doubled to 14%, and redoubled to 28%. The high level of 70% was used to see if the high level would be toxic to the plants. This was done as a result of a preliminary literature review where it was found that a plant would use 10× more zinc than copper. It was believed that this level would be toxic to the plants.

The percentage levels were calibrated by weight using grams as the weight of measure.

Mar. 14, 2000

The latex paint and ZnCl2 were measured out in grams. The ZnCl2 was mixed with the paint using distilled water to mix with the ZnCl2 to give a liquid solution to mix with the paint. Since the percent of ZnCl2 was figured by weight, paint equal to the weight of water used for zinc solution was removed in order to keep the percentages the same, this being done before the ZnCl2 was added to the paint. The amount of water added and paint removed follows: 7%–45.4 grams; 14%–45.990 grams; 28%–54.50 grams; and 70%–150.75 grams. Then the ZnCl2 was mixed with the water and then the paint and the paint was shaken in cans. Heat was produced upon solution of the components, the 70% solution being very hot to the touch.

Mar. 26, 2000

The inside surface of 20 pots were painted with each of 7% Zinc Chloride; 14% Zinc Chloride; 28% Zinc Chloride; 70% Zinc Chloride; Latex paint; and Spin Out® for a total of 120 pots. The Spin Out® and the latex paint were sprayed. Most of the 7% pots were sprayed. The remainder of the pots were painted with a sponge brush because the mixture was too thick to spray.

Mar. 30, 2000

Another coat of mixture was applied to the groups of pots with the four zinc chloride treatments, letting them dry over the weekend. The ambient humidity was very high during the application of the second coat.

Apr. 3, 2000

The plants were potted using Metro Mix 700® growing medium. The 28% and 70% Zinc chloride treatments were still wet at time of potting. Most of the 70% treated pots had most of the paint ran to the bottom of the pot.

Apr. 10, 2000

Plants were drenched with a fungicide(Subdue® and Terre Chlor®). Plants were all developing normally.

Apr. 17, 2000

Plants were checked. With the exception of two dead Vincas, the plants looked good.

Apr. 24, 2000

Plants were checked. Most looked good. There were 4 dead Vincas. The dead plants were: 1–70% ZnCl2; 1–7% ZnCl2; 1–28% ZnCl2; and 1–14% ZnCl2. Of the remaining Vincas, 23 showed signs of yellowing. Of the Impatiens, 3 showed signs of yellowing, including 1-NT; 1–28% ZnCl2; and 1–70%. All the Begonias looked good. Seven had blooms, including 1–70% ZnCl2; 2–7% ZnCl2; 2-So; and 2-NT. Of the 42 Impatiens, 40 had blooms. The two without blooms were SO treatment and Latex paint treatment, respectively. No Vincas had blooms. The plants were dry so they were watered.

May 23, 2000

Data on plants was collected, pictures taken, tissue rating and root rating were made, dry weights of tissue and roots were measured, plants were submitted for tissue analysis, and the growth index of the plants was taken with the following results:

Root Rating

The scale use for root rating is:

1. Excellent control, no roots visible.
2. Good control, root tips or stunted roots visible.
3. Poor root control, roots visible, but less than control.
4. No root control, as many roots visible as control plants.
5. No root control, more roots visible than on control plants.

The following evaluations were made as seen in Tables 2–4, below:

TABLE 2

Begonia Evaluation Results

| Plant | 7% ZnCl2 | 14% ZnCl2 | 28% ZnCl2 | 70% ZnCl2 | Latex | No Treat | S.O. |
|---|---|---|---|---|---|---|---|
| A-1 | 2 | 2 | 1 | 3 | 3 | 4 | 1 |
| A-2 | 2 | 2 | 1 | 2 | 5 | 4 | 1 |
| A-3 | 3 | 2 | 1 | 3 | 4 | 4 | 2 |
| A-4 | 3 | 2 | 2 | 3 | 5 | 4 | 1 |
| A-5 | 2 | 2 | 1 | 4 | 4 | 4 | 1 |
| A-6 | 2 | 2 | 2 | 2 | 2 | 4 | 2 |
| Avge. | 2.33 | 2.0 | 1.33 | 2.83 | 4.33 | 4.0 | 1.33 |

TABLE 3

Impatiens Evaluation Results

| Plant | 7% ZnCl2 | 14% ZnCl2 | 28% ZnCl2 | 70% ZnCl2 | Latex | No treat | S.O. |
|---|---|---|---|---|---|---|---|
| B-1 | 3 | 2 | 2 | 2 | 4 | 4 | 1 |
| B-2 | 3 | 3 | 3 | 3 | 4 | 4 | 2 |
| B-3 | 3 | 2 | 3 | 2 | 4 | 4 | 1 |
| B-4 | 3 | 3 | 2 | 3 | 3 | 4 | 1 |
| B-5 | 3 | 3 | 2 | 3 | 4 | 4 | 2 |
| B-6 | 3 | 3 | 2 | 3 | 4 | 4 | 2 |
| Avge. | 3.0 | 2.66 | 2.33 | 2.66 | 3.83 | 4.0 | 1.50 |

TABLE 4

Vinca Evaluation Results

| Plant | 7% ZnCl2 | 14% ZnCl2 | 28% ZnCl2 | 70% ZnCl2 | Latex | No treat | S.O. |
|---|---|---|---|---|---|---|---|
| C-1 | 3 | 3 | dead | 2 | 3 | 4 | 1 |
| C-2 | dead | 2 | 1 | dead | 3 | 4 | 2 |
| C-3 | 2 | 1 | 1 | dead | 5 | 4 | 1 |
| C-4 | 2 | dead | dead | 1 | 3 | 4 | 2 |
| C-5 | 3 | 2 | dead | 1 | 4 | 4 | 2 |
| C-6 | 2 | 3 | dead | 2 | 4 | 4 | 2 |
| Avge. | 2.0 | 1.83 | 0.33 | 1.0 | 3.66 | 4.0 | 1.66 |

Note: In all the species, the 28% and 70% ZnCl2 gave too much control. Roots were not formed well. Soil ball would fall apart as there were no roots to hold it together.

Root Rating Conclusion

When comparing the treatments of Zinc Chloride and Spin Out® (S.O), it was found that the S.O. treatment did the best job of root pruning. It is noted that the 7% ZnCl2 and the 14% ZnCl2 treatments performed very well. These two treatments were very comparable to the S.O. treatment. It is also important to note that the 28% ZnCl2 and 70% ZnCl2 treatments had too much root control, i.e., there was absence of roots, and the plants were not well developed.

Although the S.O. treatment did prune the roots the most, the roots that received the 7% ZnCl2 and 14% ZnCl2 had good pruning, as well as some lateral branching of the roots. The S.O. treatments had less lateral branching of the pruned roots.

Similar ratings were performed for plant tissue and flowers. When comparing the treatments for quality of tissue and flowers, it was found that the 14% ZnCl2 treatment had the best growth response in the trial. Although the plants with no treatment and the 7% ZnCl2 treatment were not far behind the 14% ZnCl2 treatment, the plants with the 28% ZnCl2, 70% ZnCl2, and the Spin Out® treatments were not close to the 14% ZnCl2 treatment.

When comparing the overall rank of the seven treatments is as follows: (1) 14% ZnCl2 treatment(1.61), (2) No treatment(1.66), (3) 7% ZnCl2 treatment(1.67), (4), Latex (1.94), (5) 70% ZnCl2 treatment(2.33), (6) S.O.(2.55), and 28% ZnCl2 treatment(3.11).

Comparisons were done for plant tissue dry weight. When comparing the treatments by dry weight, it was found that the plants with no treatment had the highest dry weight. The other treatments were all pretty close except for the 28% treatment which was the lowest. When comparing the ZnCl2 treatments to each other, It was found that the 14% treatment was the highest and the 28% ZnCl2 treatment was the lowest.

Comparisons were done for root dry weight. When comparing the treatments by root dry weight, it was found that the plants with no treatment again had the highest overall dry weight. The other treatments were all within one gram of each other. When comparing the ZnCl2 treatments to each other, It was found that 14% ZnCl2 treatment was the highest and 28% ZnCl2 was the lowest. The S.O. treatment yielded the lowest root dry weight.

Summary

In this test the 28% ZnCl2 treatment did give the best results on root pruning, but was worse in the tissue and flower ratings. When comparing all the treatments based on root pruning, tissue and flower rating, dry weights, and growth index, the recommended treatment is the 14% ZnCl2 treatment. The 14% treatment was at the tip in the tissue and flower rating, second in the dry weights, and third in the root pruning ratings. It was third only to the 28% ZnCl2 treatment and the Spin Out® treatment in root ratings. The plants treated with the 28% ZnCl2 were last in tissue and flower rating and next to last in dry weights. The plants treated with the Spin Out®, though second in the root pruning, were next to last in tissue and flower rating and last in root dry weights.

The Spin Out® does a good job of pruning the roots of the plants, but the plants treated with 14% ZnCl2 performed better overall. While pruning the roots, it also demonstrated more lateral branching which the S.O. treated plants lacked. This may have attributed to the lower performance of the S.O. treated plants in the tissue an flower ratings and the root dry weights.

EXAMPLE 2

Upon studying the previous results, it was determined that root structure as well as root control should be more carefully studied. The S.O. root control compound provides excellent root control but results in a relatively small root system which may prejudice the survival of the plant upon transplant, particularly when the plant is subjected to harsh conditions after transplant. As a result, a study was conducted employing a different standard of root rating concentrating on root development while maintaining sufficient root control.

Herbaceous plants will develop a matted root system if allowed to remain in a nursery container an extended period of time. Once transplanted into the landscape, this matted root system prevents branching of the roots into native soil. In most Mississippi summer environments, the matted root system results in poor growth and usually pre-mature death of the transplants. Test results show that Zinc chloride prevents root circling of many herbaceous plants while encouraging root branching to assist the plant in developing lateral root growth.

Procedure

Six herbaceous annuals were transplanted from 144 plug trays into 4 inch square nursery containers on Apr. 14, 2001 and placed in a heated greenhouse. The four inch black containers were used in this study with the inside walls and bottom of the containers sprayed with either 3%, 7%, and 14% of Zinc Chloride mixed in a white, water-based latex paint carrier on Apr. 4, 2001 and allowed to dry previous to the transplanting. Two types of control were used in this study: an S.O. and a not treatment control. Plants were transplanted in Premier Pro Mix BX amended with ⅓ three eights minus pine bark. The plants were transplanted into the landscape on Jun. 15, 200. Visual rating of the top growth revealed no difference in bloom size, quality, or overall size of the plant. Several plants were then removed from their containers and the roots washed, removing the root ball in order to rate the root system according to a new scale listed below. The new scale is made in response to the past studies as in Example 1, above.

Root Visual Rating Scale
1. Excellent control, no root circling, multiple lateral root growth and lateral branching of roots.
2. Good control, no root circling, some lateral root growth(3 or fewer roots, multiple lateral branching of roots.
3. Poor control, some root circling(more than 3 roots) with some lateral root growth, multiple lateral branching, large roots diameter.

TABLE 5

| Plant | Root Evaluation | | | |
| --- | --- | --- | --- | --- |
| | 3% ZnCl2 | 7% ZnCl2 | 14% ZnCl2 | Control |
| Vinca 'Pacific Orchid' | 2 | 2 | 1 | 3 |
| Impatiens 'Clean White' | 2 | 2 | 1 | 3 |
| Lantana 'Accent' | 3 | 1 | 1 | 3 |

In past studies, root circling comparisons were made with the thought of no root emerging from the soil ball as the rule, however, with the use of zinc, a different prospective of root pruning has emerged. Unlike S.O. which burns the root tip, causing death of tissue, the inventive zinc compound treatment retards development of the root tip, while encouraging lateral root development, a desirable result demonstrated by the comparative studies carried out in Example 1, and the present tests. The inventive technique of root pruning is gentle on the root system while increasing a healthy root system to absorb nutrients and water from the soil.

Characteristics of untreated container grown plants include the roots penetrating the soil volume and encircling the outside of the soil ball. This phenomenon encourages a small root system and makes the root system more susceptible to freezing temperatures. Without root through the soil substrate, nutrients and water are leached through the substrate, never being utilized by the plant. Test results employing the inventive zinc compounds encourage root branching throughout the soil substrate, not just between the outer soil ball and the inside container wall.

It is known that zinc increases the activity of indole butyric acid appears to be so in the many plants treated with various forms of zinc. The S.O. burns the root tips back from the soil surface, but as documented in this study, does not increase root mass. Another drawback of using S.O. is that it migrates into the soil while still burning the tips of roots of the plant. The objective of this study is to investigate treatments which decrease the root circling while promoting root branching.

It was observed on Vinca that the higher the zinc chloride concentration in the carrier, the more root mass observed. This was observed in all treatments of zinc, however the most obvious was the 14% treatment. The higher zinc treatments resulted in more root branching, thus increasing the root mass, capable of absorbing nutrients and water. In Vinca, the 14% zinc treatment reflected the largest root system of the various treatments.

The results were very well branched, having thousands of fine feeder roots. Roots penetrating the outside of the soil ball appear well branched and did not circle the outside of the soil ball. This is important because the natural and common growth pattern of container plants is for the root system to emerge from the soil substrate and begin circling between the outer edge of the soil ball and the inside wall of the container. This treatment has the unexpected result of not only preventing root circling but increasing root mass.

When roots become matted with roots circling the outer edge of the root ball, this condition is referred to as a "pot bound" plant. The S.O. treatment showed no roots penetrating the outer soil ball but the roots were not well developed and thus were not evaluated on the visual scale. This is the most obvious differences between copper and zinc treatments. Copper in S.O. appears to burn the root tip back, pruning the root to prevent emergence from the soil ball, while the inventive zinc compounds as applied do not burn the root tip, but increases natural occurring hormones within the plant root, causing massive cell division while preventing roots from circling. This was observed when comparing the root systems resulting from the 14% zinc treatment and the S.O. treatment. The smaller root system of the S.O. treatment would be less able to survive in a hostile environment.

As can be seen in Table 5, the 14% zinc chloride in binder is rated in category 1 under the visual root rating scale in three plant species and is thus considered the preferred composition under these test conditions. However, as little as 3% zinc chloride in binder provides an acceptable category 2 rating in two of the three plant species as compared to the control plants rated as category 3 with unacceptable root circling and large root diameter. The 7% Zinc Chloride in binder provides at least an acceptable category 2 rating. The 3% Zinc Chloride in binder results illustrate that a concentration in this range gives useful results for the purpose described for at least some species.

There were no observable differences in top growth from any treatments. This can be said of all treatments and plants. The tops, in most situation appears to be about the same in size, flowers, and color. However, once the root system is exposed, the differences in root system is abundantly clear. These differences appear to be the primary difference resulting from the use of S.O. and the inventive zinc compounds. Zinc treatments repeatedly showed a greater root mass without allowing the roots to circle the outside of the soil ball. This is a clear asset to the grower, landscaper, and homeowner.

Based on the results of this test, it is concluded that Zinc Chloride within the range of about 3% and 14% zinc by weight in binder is useful to prune the roots of bedding plants effectively. Previous studies as in Example 1 illustrate the usefulness of Zinc Chloride up to an upper limit of about 28% zinc. Although the S.O. product is effective, the Zinc Chloride within the range of about 3% to about 28% rate produced healthier or acceptable plants based on the above research. The preferred demonstrated rate is about 14% Zinc Chloride. By using a zinc compound such as Zinc Chloride we are also helping our environment by making it possible to use recycled automobile tires as a source of the zinc.

The present invention is not limited to any particular binder or carrier. The white latex paint was chosen due to its low cost and convenience of use, but many other binders or carriers, such as corn starch, may be used for the elemental Zn and Zn compounds of the present invention.

The use of elemental zinc, and any or all zinc compounds, such as zinc oxide, and zinc sulfate, zinc oxide carbonate, and zinc hydroxide are contemplated in the inventive root control composition of the present invention. The zinc chloride, as demonstrated in the above example, appears most useful for bedding plants in small nursery pots which requires root control effectiveness over a short period of time such as about six weeks. Zinc oxide has a much slower release time from the binder and would be more useful where root control is desired over a long period of time.

The range of zinc concentration in the carrier is preferably about 14% as demonstrated in the above example, but the 3% and 7% zinc concentration was also demonstrated to be effective, and the composition is useful up to about 28%, where too much root control is accomplished.

It is to be understood that the present invention is not limited to the embodiments described above, but encompasses any and all embodiments within the scope of the following claims.

We claim:

1. A root control composition, comprising:
   a zinc-based material selected from the group consisting of metallic zinc and a compound of zinc in an amount effective for encouraging branching of plant roots and preventing root circling in a container; and
   a binder.

2. The root control composition of claim 1, wherein the effective amount of said zinc-based material is within the range of about 3 weight percent to about 28 weight percent of the composition.

3. The root control composition of claim 1, wherein said compound of zinc is selected from the group consisting of zinc oxide, zinc chloride, zinc sulfate, zinc oxide carbonate, and zinc acetate.

4. The root control composition of claim 1, wherein said compound of zinc is zinc chloride.

5. The root control composition according to claim 1, wherein said compound of zinc is an inorganic salt.

6. The root control composition of claim 1, wherein said compound of zinc is zinc chloride. wherein the effective amount of said zinc-based material is about 14 percent by weight of the composition.

7. The root control composition of claim 1, wherein said binder is latex paint.

8. A method for treating a nursery pot for root control, comprising the steps of:

forming a composition including elemental zinc or a compound thereof in an amount effective for encouraging branching of plant roots and preventing root circling in a container, and a binder; painting an interior of the pot with said composition; and allowing the composition to dry.

9. The method of claim 8, wherein the amount of said elemental zinc or zinc compound in the composition is within the range of about 3 weight percent to about 28 weight percent.

10. The method of claim 9, wherein the amount of said elemental zinc or zinc compound in the composition is about 14 weight percent.

11. The method of claim 9, wherein said binder is latex paint.

12. The method of claim 9, wherein said compound of zinc is zinc chloride.

13. An article of manufacture, comprising a root control nursery pot having an interior coated with a root control composition, wherein the composition includes:

a zinc-based material selected from the group consisting of metallic zinc and a compound of zinc in an amount effective for encouraging branching of plant roots and preventing root circling in a container; and a binder.

14. The article of manufacture of claim 13, wherein the effective amount of said zinc-based material in said composition is within the range of about 3 weight percent to about 28 weight percent.

15. The article of manufacture of claim 13, wherein the effective amount of said zinc-based material in said composition is about 14 weight percent.

16. The article of manufacture of claim 13, wherein said binder is latex paint.

* * * * *